United States Patent [19]

Campbell et al.

[11] Patent Number: 5,021,654
[45] Date of Patent: Jun. 4, 1991

[54] ALL CERAMIC ION MOBILITY SPECTROMETER CELL

[75] Inventors: Donald N. Campbell, Lake Jackson, Tex.; Glenn E. Spangler, Lutherville; Robert C. Davis, Jr., Westminster; Eugene F. Fafaul, Phoenix; John P. Carrico, Jr., Baltimore, all of Md.

[73] Assignee: Environmental Technologies Group, Inc., Baltimore, Md.

[21] Appl. No.: 344,917

[22] Filed: Apr. 28, 1989

[51] Int. Cl.$^5$ ............................................. H01J 49/40
[52] U.S. Cl. ................... 250/287; 250/286; 250/281
[58] Field of Search ........... 250/287, 286, 281, 396 R, 250/505.1; 313/363.1, 404, 269, 451, 456, 348

[56] References Cited

U.S. PATENT DOCUMENTS

| | | | |
|---|---|---|---|
| 3,370,192 | 2/1968 | Schwartz et al. | 313/404 |
| 4,390,784 | 6/1983 | Browning et al. | 250/287 |
| 4,633,083 | 12/1986 | Knorr et al. | 250/287 |
| 4,712,008 | 12/1987 | Vora et al. | 250/287 |

Primary Examiner—Jack I. Berman
Attorney, Agent, or Firm—Leonard Bloom

[57] ABSTRACT

An ion mobility spectrometer is described for detecting sample gas in a carrier gas incorporating a block of ceramic material having a passageway wherein the passageway contains an ionization s.. .e, a resistive material on the walls of the passageway prior to and after a shutter grid to form a reaction region and drift region respectively, an aperture grid and a collector. A radioactive or non-radioactive ionization source may be inserted into one end of the passageway while the aperture grid and collector may be inserted into the other end and rigidly positioned with respect to the block of ceramic material. The invention simplifies the exchange of the ionization sources where it may be either radioactive or non-radioactive, and improves the assembling and sealing of the ion mobility spectrometer cell.

30 Claims, 8 Drawing Sheets

ALL CERAMIC ION MOBILITY SPECTROMETER CELL

CROSS REFERENCE TO A RELATED APPLICATIONS

Cross reference is made to U.S application Ser. No. 701,898 filed on Feb. 15, 1985, now U.S. Pat. No.4,839,143, entitled "Selective Ionization of Gas Constituents Using Electrolytic Reactions" by K.N. Vora et al. and assigned to the assignee herein which is directed to an electrolytic ionization source using inorganic/organic salts for use in an ion mobility spectrometer, an ionization detector and a mass spectrometer.

Cross reference is made to U.S. application Ser. No. 319,549 filed on Mar. 6, 1989, entitled "Selective Ionization of Gas Constituents Using Electrolytic Reactions" by K.N. Vora et al. and assigned to the assignee herein which is a divisional application of the above cross referenced application, Ser. No. 701,898 filed on Feb. 15, 1985, and is directed to methods for ionization using inorganic/organic salts for use in an ion mobility spectrometer, an ionization detector and a mass spectrometer.

BACKGROUND OF THE INVENTION

1. Field of the Invention

This invention relates to ion mobility spectrometers and more particularly to an all ceramic ion mobility spectrometer detector cell.

2. Description of the Prior Art

The technique of ion mobility spectrometry (IMS) originally called plasma chromatography was disclosed in the early 1970's in order to analyze and detect organic vapors. A typical ion mobility spectrometer (IMS) detector cell consists of a reaction region for generating ions and a drift region for measuring the mobility of the ions. The reaction region and the drift region are separated by a shutter grid which functions to gate the ions from the reaction region into the drift region. An inlet duct provides a gas to the reaction region. In the reaction region an ionization source, for example, tritium, $63_{Ni}$, $241_{Am}$, etc. ionizes some of the gas. An electric field in the reaction region moves the ions towards the shutter grid. The ions are gated into the drift region where their mobility is measured by their arrival times at a collector at the far end of the drift region. The drift region is biased with an electric field to move the ions towards the collector. The drift region may have a drift gas flowing therein from the collector towards the shutter grid.

In U.S. Pat. No. 4,712,008 which issued on Dec. 8, 1987 to K.N. Vora et al. and assigned to the assignee herein, a ion mobility spectrometer is described incorporating a cylindrical tube which may be ceramic containing a reaction region, a shutter assembly and a drift region therein, the cylindrical tube fits within a housing having a chamber or space between the cylindrical tube and the housing for heating drift gas prior to entry into the drift region. Further, the cylindrical tube may have interior annular ledges to facilitate positioning of the shutter assembly and an aperture grid.

One example of a means for providing an electric bias field in the drift region as well as the reaction region is provided in U.S. Pat. No. 4,390,784 which issued on June 28, 1983 to D.R. Browning et al. and assigned to the assignee herein. In U.S. Pat. No. 4,390,784 a ceramic tube is disclosed with a coating on its inside surface of a thick film resistor. A voltage potential is placed across the film in the longitudinal direction of the drift region to provide a longitudinal electric field from the shutter grid to the collector.

In U.S. Pat. No. 4,445,038 which issued on Apr. 24, 1984 to G.E. Spangler and J.F. Wroten, Jr. and assigned to the assignee herein, an ion mobility detector is described having dual drift regions respectively on either side of a centrally located reaction region and respectively separated from the reaction region by dual shuttered grids.

An improvement to the inlet of gas to the reaction region is described in U.S. Pat. No. 4,311,669 which issued on Jan. 19, 1982 to G.E. Spangler entitled "Membrane Interface for Ion Mobility Detector Cells" which is assigned to the assignee herein. The U.S. Pat. No. 4,311,669, a membrane interface is provided over the sample inlet port of an ion mobility detector. The sample penetrates the membrane and is carried into the ion mobility detector by means of a carrier gas which scrubs the interior surface of the membrane.

Another improvement to the inlet of gas into the reaction region is described in U.S. Pat. No. 4,378,499 which issued on Mar. 29, 1983 to G.E. Spangler et al. which is assigned to the assignee herein entitled "Chemical Conversion for Ion Mobility Detectors Using Surface Interactions" In U.S. Pat. No. 4,378,499 the inlet gas including a sample is passed through a catalytic reactive filter prior to injection into the reaction region of an ion mobility spectrometer to enhance selectivity and sensitivity by converting through surface interactions sample gas or vapor to a form more readily ionized or by converting through surface interactions interferent gas or vapor to a form less readily ionized. Alternatively, the inlet gas may be exposed to a reactive coating placed on the surface of a permeable membrane prior to diffusion therethrough into the reaction region or exposed to a reactive coating placed on the interior walls of the reaction region. The reaction region is formed by a plurality of conductive rings and a drift region formed by a plurality of conductive rings with drift gas entering near the detector and being exhausted near the shutter grid.

SUMMARY OF THE INVENTION

An ion mobility spectrometer is described for detecting a sample gas or constituent in a carrier gas comprising a block of ceramic material having a passageway therethrough containing a reaction region, a shutter grid, a drift region, an aperture grid, and a collector; the passageway has a longitudinal axis and a first length to form a reaction region beginning at a first end of the first length and extending to a shutter grid; the passageway having a cross section from its first end for receiving and supporting an ionization source positioned in the reaction region; the first length of the passageway having portions thereof with a first resistive layer therein to provide an electric field in the direction of the longitudinal axis when a voltage is placed longitudinally across the first resistive layer to move ions formed in the first length to the shutter grid, the shutter grid positioned across the passageway at the second end of the first length; the passageway having a second length to form a drift region extending from the shutter grid to an aperture grid, the second length of the passageway having portions thereof with a second resistive layer thereon to provide an electric field in the direction of the longitudinal axis when a voltage is placed longitudinally across the second resistive layer to move ions passing through the shutter grid to the aperture grid, the aperture grid positioned across the passageway at the second end of the second length, the passageway having a third length having a first and second end extending from the aperture grid to a collector respectively; the passageway having a cross section from its second end of the passageway for receiving the aperture grid for positioning at the first end of the third length and for receiving the collector for positioning at the second end of the third length; first means for introducing a drift gas into the drift region; and second means for introducing a carrier gas including a sample gas to be detected into the reaction region.

The invention further provides an ion mobility spectrometer which does not require a separate housing to hold and support components forming the reaction region and drift region.

The invention further provides an all ceramic Ion Mobility Spectrometer which eliminates the problems associated with outgassing and sample hang-up when plastic and polymeric materials are used.

The invention further provides shielding from electromagnetic interference (EMI) within the reaction region and drift region by utilizing a resistive layer on the inside surfaces of the reaction region and drift region.

The invention further provides a low cost ion mobility spectrometer which may have a reaction region and drift region machined from machinable ceramic known as Macor, or molded and/or cast and subsequently fired in alumina.

The invention further provides the feasibility of providing heaters in or on the outside of the ceramic material for heating the drift gas, the carrier gas, the reaction region and the drift region. The heaters may be provided by resistive layers in the form of thick films applied to the outside surfaces of the ceramic material.

The invention further provides a mechanically convenient method for replacing the ionization source.

The invention further provides a mechanically convenient method for interchanging the ionization source from a non-radioactive source for example a thermionic source in the form of a bead of beta alumina to a radioactive source for example $^{63}$Ni.

The invention in one embodiment further provides a method for installing a shutter grid without altering the cross section of the passageway.

The invention further provides a simple technique for forming a shutter grid across the passageway to separate the reaction region from the drift region.

The invention further provides an aperture with positive anchoring means to prevent mechanical vibration of the aperture.

The invention further provides a collector rigidly mounted within a ceramic block which may be inserted into the passageway and against the aperture grid at its periphery to prevent relative movement between these two electrodes and to prevent microphonics in the collector.

The invention further provides an ion mobility formed from a single block of ceramic for more uniform thermal expansion, said ion mobility spectrometer being capable of operating at temperatures above room temperature for example 100° C. while sealed to have a leak rate below $10^{-7}$ cubic centimeters per second of helium.

DETAILED DESCRIPTION OF THE PREFERRED EMBODIMENTS

Figure 1:
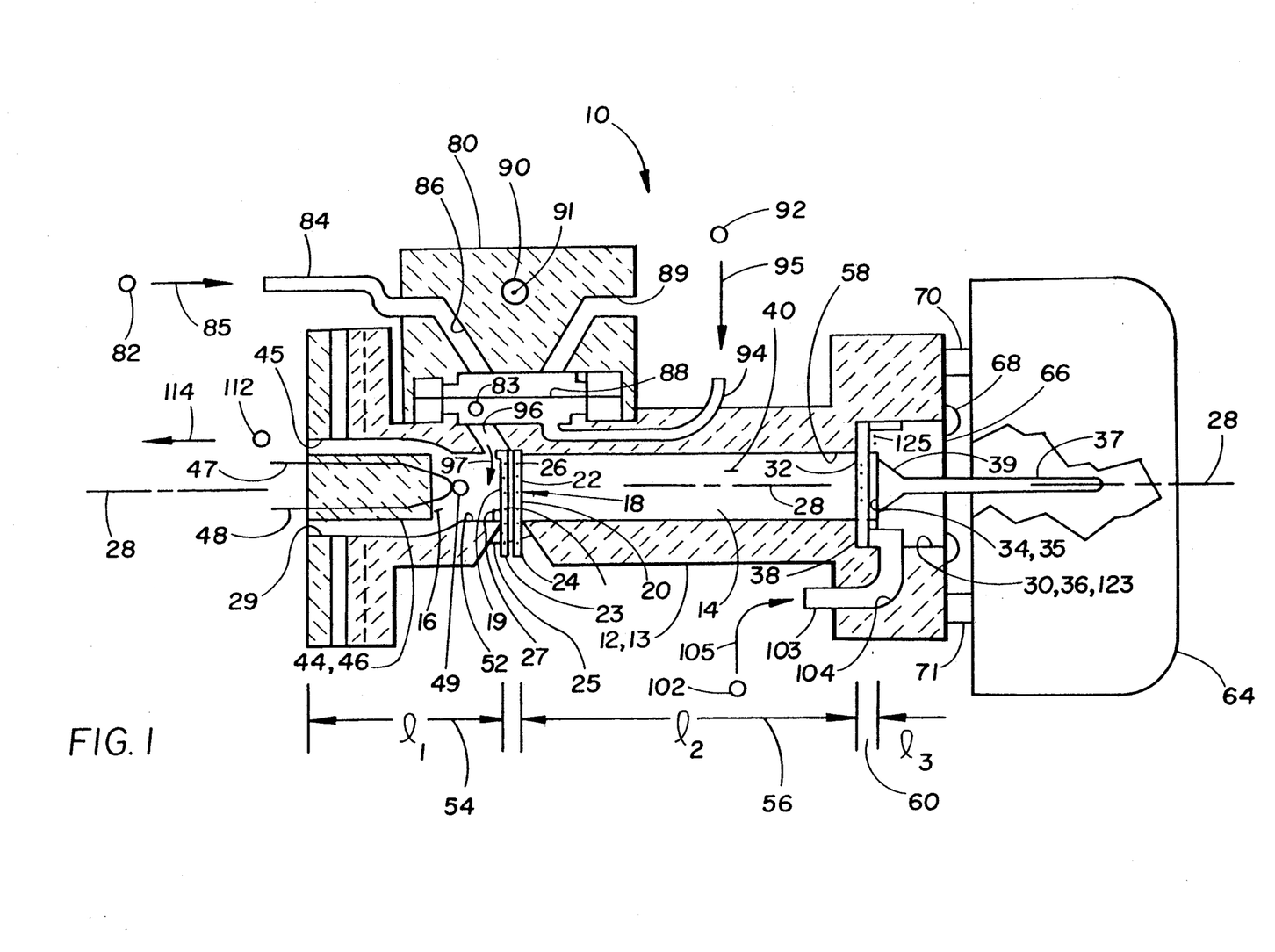
FIG. 1 is one embodiment of the invention having a shutter grid assembly and a non-radioactive ionization source.

Referring to FIG. 1, an ion mobility spectrometer (IMS) 10 is shown. A block of ceramic material 12 has a passageway 14 therethrough containing a reaction region 16, a shutter grid assembly 18 comprising a first shutter grid 19 and a second shutter grid 20 which are spaced apart by spacer 21. Spacer 21 may be for example a ceramic washer. Shutter grids 19 and 20 may be for example stainless steel or other suitable metal etched to form 0.076 mm (0.003 inches) wires 22. First shutter grid 19 has tab 23 and second shutter grid 20 has tab 24 extending through the block of ceramic material 12 to allow electrical connection from the outside. A high temperature adhesive such as epoxy cement EA 934 manufactured by Hysol Division, The Dexter Corporation, Pittsburgh, CA, or a ceramic adhesive manufactured by Cotronics and AREMCO may be used to seal passageway 14 from leaks where tabs 23 and 24 pass through the block of ceramic material 12. Adhesive 25 is shown applied between tabs 23, 24 and block ceramic material 12.

Passageway 14 has a longitudinal axis 28 passing through the center of the passageway which may be for example cylindrical having an equal or larger diameter at a first end 29 and at a second end 30 than drift region 40. The passageway 14 also has an aperture grid 32 and a collector 34 positioned in well 36 of passageway 14 which forms an annular ledge 38 with the drift region 40 between shutter grid assembly 18 and aperture grid 32. Reaction region 16 may be formed in passageway 14 in a first length of passageway 14 from first end 29 to shutter grid assembly 22. Passageway 14 has a sufficient cross section at the first end for receiving and supporting an ionization source 44. Ionization source 44 may consist of a ceramic plug 46 having slots 45 therein for passing exhaust gas 112 out the first end 29. Ceramic plug 46 may include holes for passing wires 47 and 48 therethrough to a thermionic emitter 49 which may be for example beta alumina.

The first length $l_1$ of passageway 14 may have portions thereof with a first resistive layer 52 thereon to form an electric field in the direction of longitudinal axis 28 across the resistive layer to move ions formed in the first length to shutter grid assembly 18. Shutter grid assembly 18 is positioned across passageway 14 and forms the second end of the first length $l_1$ shown by arrow 54.

Shutter grid assembly 18 may be positioned and held in place by an annular ledge 26 formed between first and second lengths by passageway 14 having a larger cross section diameter in the first length. A ceramic cylinder 27 may be inserted and pressed or cemented in place against shutter grid assembly 18 on one side with the annular ledge 26 or another cylinder 26 on the other side.

Passageway 14 has a second length $l_2$ shown by arrow 56 to form a drift region 40 extending from shutter grid assembly 18 to aperture grid 32. The second length $l_2$ of passageway 14 is drift region 40 and has portions thereof with a second resistive layer 58 thereon to form an electric field in a direction of longitudinal axis 28 when a voltage is placed longitudinally across second resistive layer 58 to move ions passing through shutter grid assembly 18 to aperture grid 32. Aperture grid 32 is positioned across passageway 14 at the second end of the second length $l_2$ shown by arrow 56. Passageway 14 has a third length $l_3$ as shown by arrow 60 having a first and second end extending from aperture grid 32 to collector 34, respectively.

Passageway 14 has a cross section from its second end 30 for receiving aperture grid 32 for positioning at the first end of the third length $l_3$ as shown by arrow 60 and for receiving collector 34 for positioning at the second end of the third length shown by arrow 60.

Collector 34 may be made of stainless steel or other suitable metal having a cone or flat section with a polished surface 35 facing aperture grid 32 and a stem 37 of a diameter extending from the cone portion 39 into an electrometer 64. Collector 34 may be supported by a ceramic block 66 which is machined or pre-formed to receive collector 34 which may be cemented or brazed to ceramic block 66. Ceramic block 66 has portions thereof pressing against the outer periphery of aperture grid 32 to hold aperture block grid 32 and collector 34 in a rigid position with respect to one another and to block ceramic material 12. Ceramic block 66 can be for example cylindrical in shape to fit into well 36 and may be sealed by a bead of adhesive 68. Electrometer 64 is rigidly positioned with respect to block of ceramic material 12 by spacers 70 and 71 and bolts therein.

A ceramic block 80 is positioned against and sealed with block of ceramic material 12 to provide a means for introducing a carrier gas 92 including a sample gas 83 into reaction region 16. Sample gas 82, for example, ambient air with constituent vapors, passes through inlet tube 84 as shown by arrow 85 into a passageway 86 in ceramic block 80 to one side of membrane 88 which may be dimethylsilicone and out passageway 89. Ceramic block 80 may have an additional passageway 90 with a cartridge heater 91 therein for heating ceramic block 80 and sample gas 82. Carrier gas 92 passes through inlet tube 94 as shown by arrow 95 to scrub the other side of membrane 88 to carry sample gas 83 which are traces or constituents of gas 82 passing through membrane 88 and through passageway 96 as shown by arrow 97 into reaction region 16.

A drift gas 102 flows through inlet tube 103 and passageway 104 as shown by arrow 105. Drift gas flows through slots or grooves 125 in ceramic block 66 into the region between collector 34 and aperture 32. Drift gas 102 flows through aperture 32 into drift region 40 and passes through shutter grid assembly 18 through reaction region 16 along with carrier gas 92 through grooves or slots 45 in ceramic plug 46. Drift gas 102, carrier gas 92 and sample gas 83 which is not ionized is shown as exhaust gas 112 exiting first end 29 as shown by arrow 114.

Block of ceramic material 12 may have conductive and resistive thick film coatings applied to the exterior surface 13 for heater elements, electrical contact pads, EMI reduction, and electrical interconnection. Holes from the exterior surface 13 to passageway 14 may be metalized or coated with conductive ink or thick film material to establish electrical contact with linear resistors in reaction 16 and drift region 40.

Figure 2:
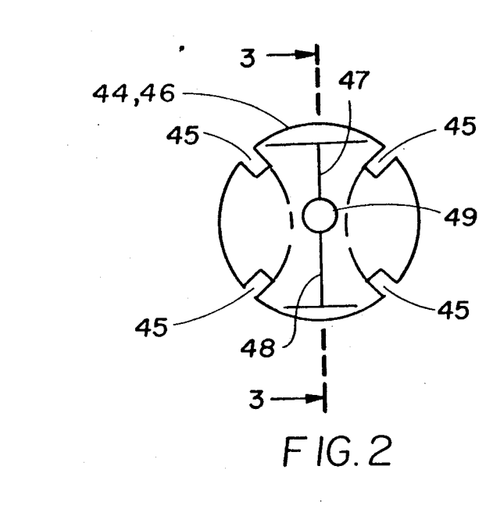
FIG. 2 is a front view of the bead assembly.

FIG. 2 is a front view of ionization source 44 showing ceramic plug 46, slots 45 for exhaust gas 112 to flow through, thermionic emitter 49 and wires 47 and 48. The dimensions of ceramic plug 46 are adjusted to fit snugly in passageway 14 at a predetermined depth and may be sealed at its periphery by a bead of adhesive 72.

Figure 3:
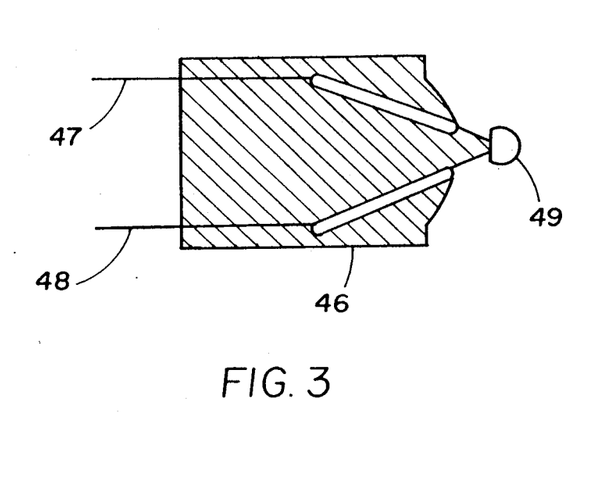
FIG. 3 is a cross section view along the lines 3—3 of FIG. 2.

FIG. 3 is a cross section view along the lines 3—3 of FIG. 2. FIG. 3 shows the structure or shape of ceramic plug 46 more clearly.

Figure 4:
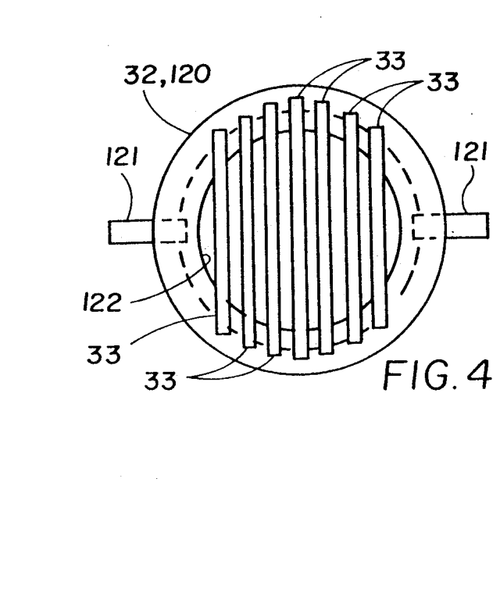
FIG. 4 is a front view of an aperture grid.

FIG. 4 is a front view of an aperture grid 32. FIG. 4 shows wires 33 which may be for example resistive wires made from an alloy of nickel and chromium having a diameter of 0.076 mm (0.003 in.). In addition to wires 33 which may be etched in or welded to washer 120, stainless steel wire 121 may be welded radially to washer 120 with tabs or lengths of wire 121 extending beyond the outer periphery of washer 120 which may be cut at a uniform length and ground or cut at an incline for example 45° across so that the rear portion of the wires is longest. The wires 121 are spot welded to the rear side of washer 120. The stainless steel wires may have a diameter for example of 0.0457 cm (0.018 in.).

Figure 5:
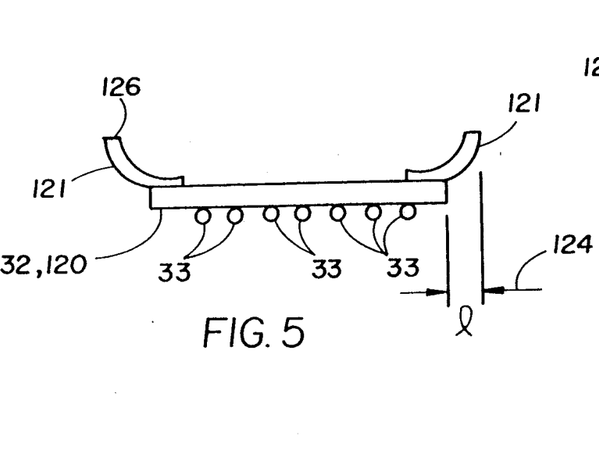
FIG. 5 is a top view of the aperture grid shown in FIG. 4.

FIG. 5 is a top view of aperture grid 32 shown in FIG. 4. When aperture grid 32 is inserted from second end 30 into passageway 14 to its correct position for example against annular ledge 38 shown in FIG. 1, wires 121 deflect slightly and scrape along the side wall of passageway 14 preventing aperture grid 32 from movement in the reverse direction towards end 30. When aperture grid 32 is seated against annular ledge 38, wires 121 function to grip the side walls of passageway 14 to hold aperture grid 32 firmly in place. Mechanical vibration of aperture grid 32 is thereby reduced. As shown in FIG. 4 washer 120 has an opening 122 to permit ions to pass through to collector 34 and to permit drift gas 102 to pass through in the opposite direction to drift region 40. Aperture grid 32 is coupled to a conductive line for placing a voltage for example in a range from 0 to 40 volts on aperture grid 32. A resistive layer 123 may coat the side walls of passageway 14 from the beginning of the third length to the second end 30 of block of ceramic material 12. When the aperture grid 32 is inserted into well 36, passageway 14, the wire protrusions 121 dig into resistive layer 123 to make electrical contact and to constrain aperture grid 32 from mechanical vibration.

Figure 6:
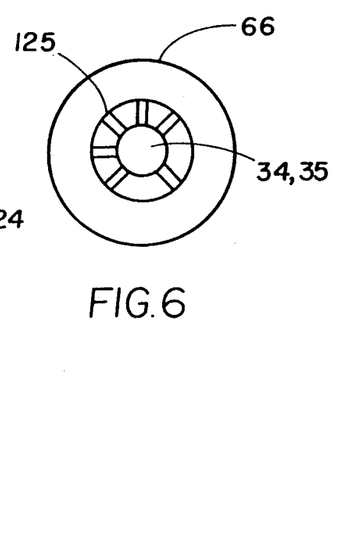
FIG. 6 is a front view of the collector and ceramic block.

FIG. 6 is a front view of collector 34 and ceramic block 66 which functions to rigidly hold collector 34 and to press against aperture grid 32 which in turn presses against annular ledge 38 of block of ceramic material 12 to form a rigid structure free of vibration. Drift gas 102 flows through passageway 104 through slots 125 shown in FIG. 6 to the region above between collector 34 and aperture 32. Surface 35 of collector 34 is polished. Slots 125 in ceramic block 66 may be seven in number and be 0.635 mm wide (0.025 in.) wide and 0.508 mm (0.020 in.) deep.

Figure 7:
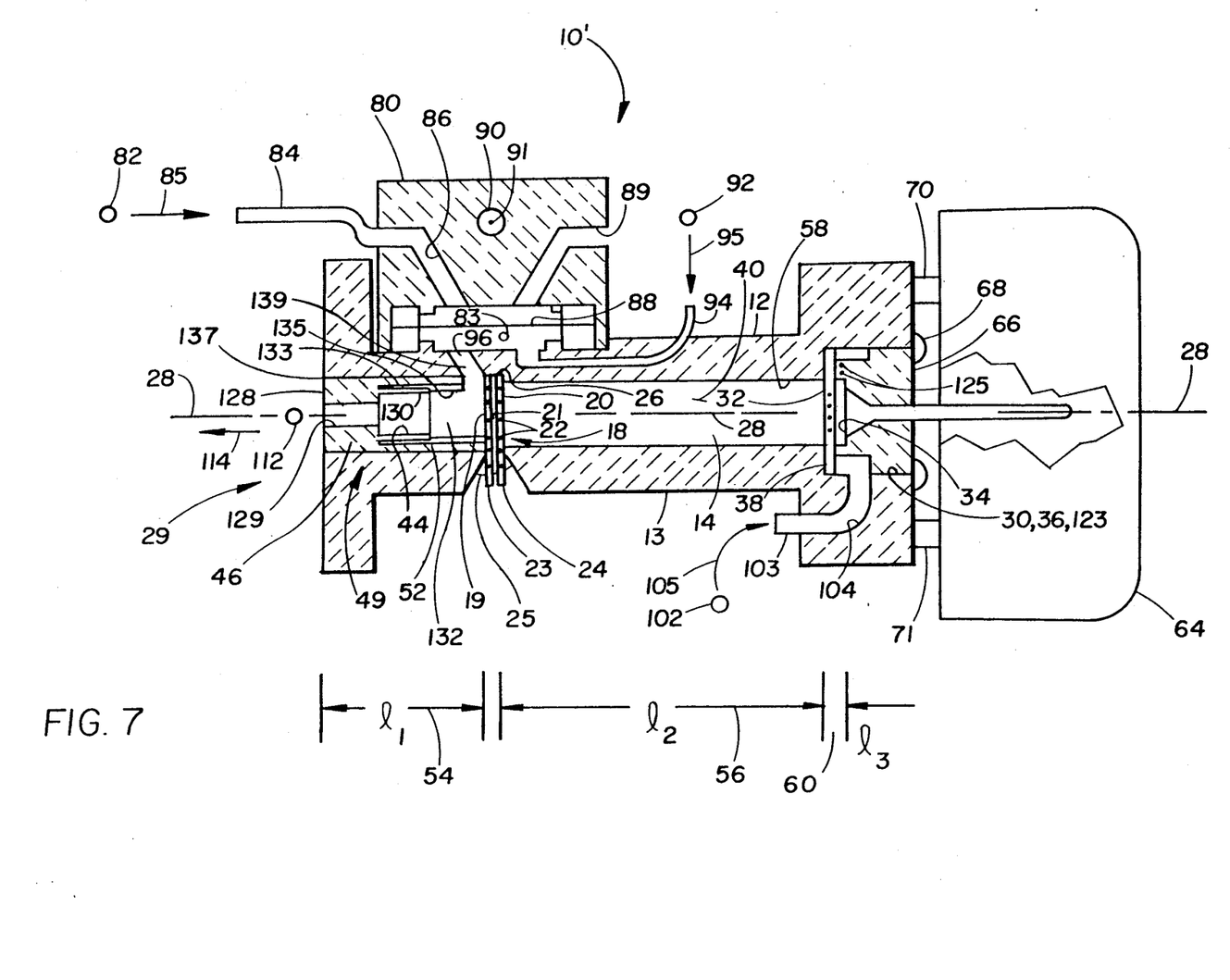
FIG. 7 is a first alternate embodiment of the invention having a shutter grid assembly and a radioactive ionization source.

FIG. 7 is a first alternate embodiment of the invention showing an IMS 10' having a shutter grid assembly 18 and an ionization source 44' which may be metal foil 130 of $^{63}$Ni. As shown in FIG. 7 a ceramic block 128 has a passageway 129 which is adjusted in size to provide a path for exhaust gas 112. As shown in FIG. 7 passageway 129 is enlarged to provide a reaction region 132. Ceramic block 128 is adjusted in length to provide at its periphery contact with shutter grid assembly 18 to hold shutter grid assembly 18 against annular ledge 26. The inside wall of reaction region 132 may contain a resistive layer 133 which may be coupled over conductive ink paths to pads for placing a voltage across resistive layer 133 and to provide an electric field parallel to longitudinal axis 28. An insulator for example a cylinder or other shape 135 conforming to the inside walls of passageway 129 may be inserted into reaction region 132. Cylinder 135 may contain radioactive foil 130 which itself may be a cylinder conforming to the inside walls of cylinder 135. Ceramic block 128 may be sealed by an adhesive 137 as shown in FIG. 7. Ceramic block 128 may be removed and replaced with another ceramic block 128 identical thereto. Removal of ceramic block 128 also removes ionization source 44' at the same time. Ceramic block 128 has outside dimensions to fit firmly in passageway 14. Ceramic block 128 contains a passageway 139 adjacent passageway 96 to permit gas 83 to enter reaction region 132 and to exhaust by way of passageway 129 out of first end 29 of passageway 14 as exhaust gas 112 as shown by arrow 114.

Figure 8:
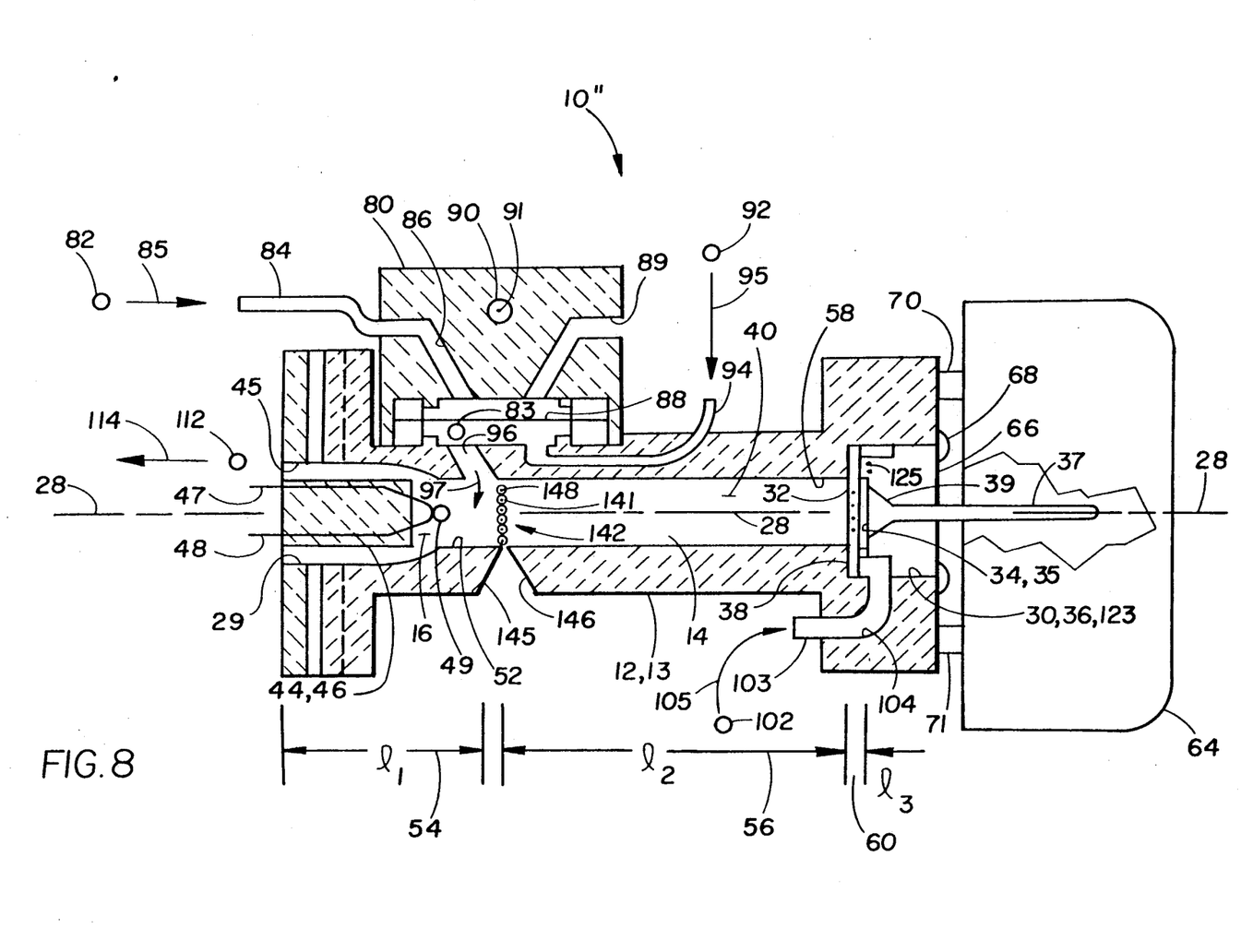
FIG. 8 is a second alternate embodiment of the invention having a planar wire shutter grid and non-radioactive ionization source.

FIG. 8 is a second alternate embodiment of the invention showing an IMS 10' having a planar wire shutter grid 142 and non-radioactive ionization source 44. In FIG. 8 like references are used for functions corresponding to the apparatus of FIG. 1. In place of shutter grid assembly 18, block of ceramic material 12 has a plurality of holes 141 drilled through with the holes spaced apart to permit wires to be fed through the holes to form shutter grid 142. By placing the holes 141 in a straight row, a planar Bradbury Nielsen type of shutter grid is constructed where every other wire may go to tab 145 and the remaining wires go to tab 146. Holes 141 may be for example 0.33 mm (0.013 in.) in diameter and spaced 0.508 mm (0.020 in.) apart. The wires used for shutter grid 142 may be 0.076 mm (0.003 in.) in diameter and an alloy of nickel and chromium with or without gold plating on the outside surface. Tabs 145 and 146 may be metalized using conductive ink to allow soldering of the wires 148 to tabs 145 and 146.

U.S. Pat. No. 4,712,008 which issued on Dec. 8, 1987 and assigned to the assignee herein is incorporated by reference to show and describe conventional details in the apparatus, the electronics, and the operation of ion-mobility spectrometer 10". Where ionization source 44 has a thermionic emitter 49, a current source must be provided to pass current over wires 47 and 48 to heat up thermionic emitter to its operating temperature.

Figure 9:
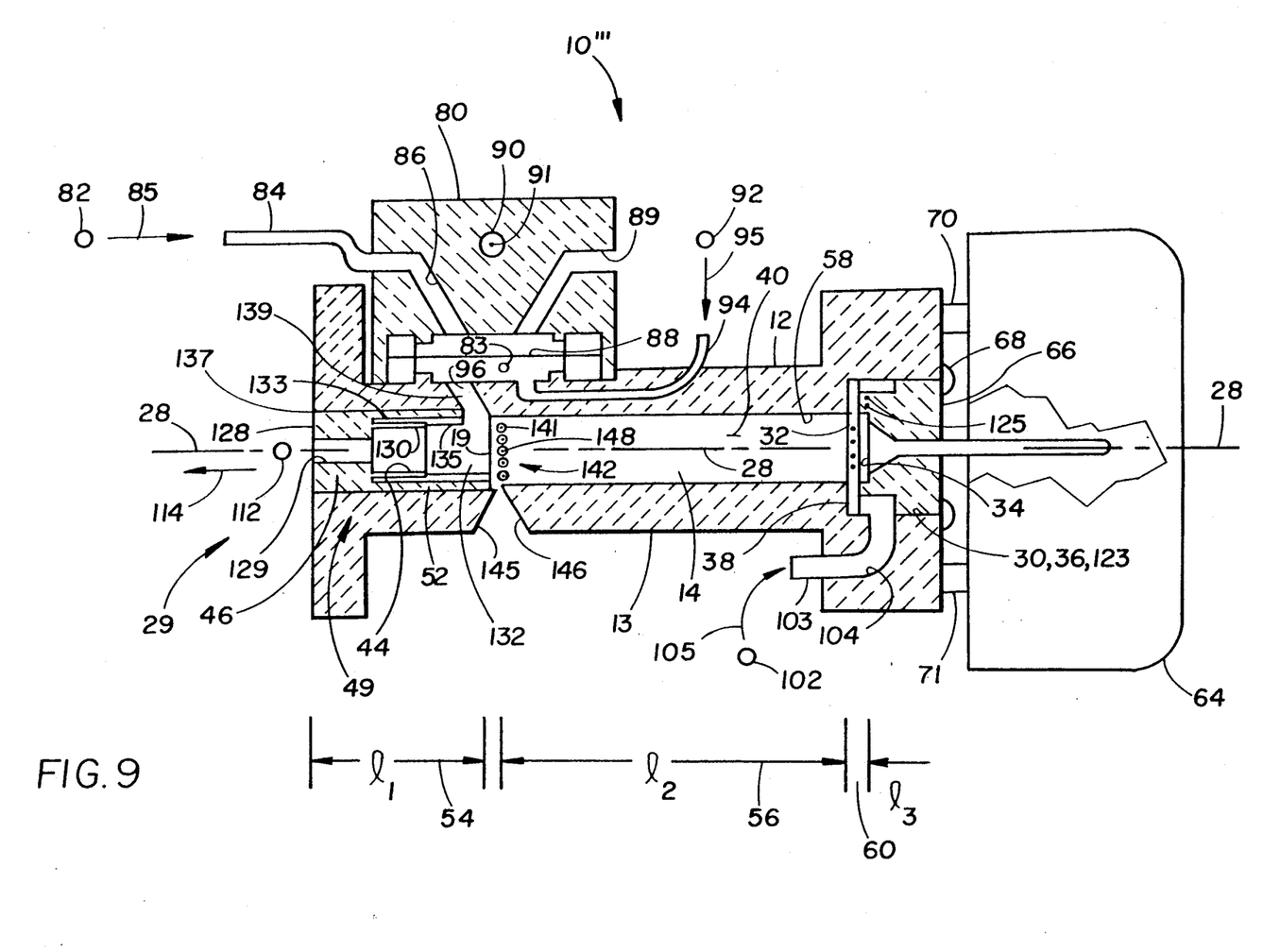
FIG. 9 is a third alternate embodiment of the invention having a planar wire shutter grid and radioactive ionization source.

FIG. 9 is a third alternate embodiment of the invention showing an IMS 10" having a planar wire shutter grid 142. In FIG. 9 like references are used for functions corresponding to the apparatus of FIGS. 7 and 8. In FIG. 9 an ionization source 44 utilizing foil 130 is shown along with utilizing shutter grid 142.

The inside surfaces of passageway 14 and 129 exposed to sample may be coated with tetrafluoroethylene (TFE) to prevent absorption of sample molecules on the inside walls of passageway 14 or on passageway 129.

An all ceramic ion-mobility spectrometer cell has been described comprising a passageway 14 which has been drilled, machined, molded, or cast therethrough to provide for the assembly of an ionization source (44, 44'), shutter grid (18, 142), aperture grid 32 and collector 34 therein which in turn forms a reaction region (16, 132) and drift region 40 for the formation and measurement of ion-mobility, respectively. Ionization sources including a thermionic emitter 49 may be mounted on a ceramic block plug 46 which may be easily inserted and removed from a first end 29 of passageway 14. At the second end 30 of passageway 14, aperture grid 32 and collector 34 which has been attached or cemented rigidly to ceramic block 66 may be inserted and removed easily. Further aperture grid 32 and collector 34 are rigidly mounted within passageway 14 to prevent mechanical vibration, which leads to microphonic noise and at the same time permit inlet of drift gas 102 through ceramic block 66 between aperture grid 32 and collector 34. In an alternate embodiment shutter grid 142 consists of wires 140 threaded through holes 141 in a block of ceramic material 12. The holes 141 pass through passageway 14 to provide a planar shutter grid 142.

Figure 10:
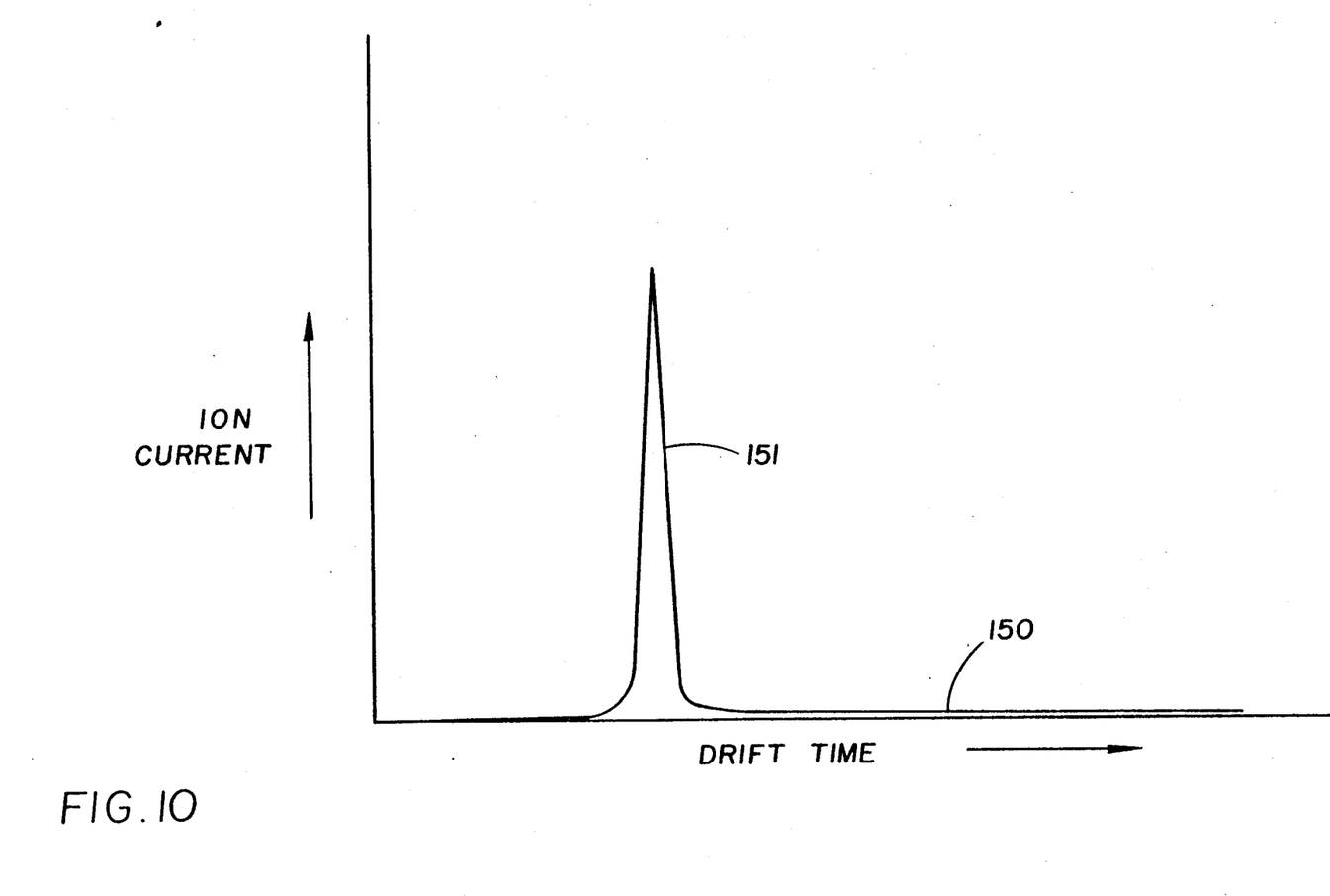
FIG. 10 is a graph showing the operation of the embodiments in FIGS. 1 and 8.

FIG. 10 is a showing the operation of IMS 10 and 10" in FIGS. 1 and 8 respectively. In FIG. 10 the ordinate represents ion current and the abscissa represents ion drift time. Ion mobility spectrum or curve 150 collected from IMS cells 10 and 10" contains an ion mobility peak 151 which is due to the positive reactant ions obtained from the non-radioactive source, i.e. a thermionic emitter of alkali cations, without sample gas 82.

Figure 11:
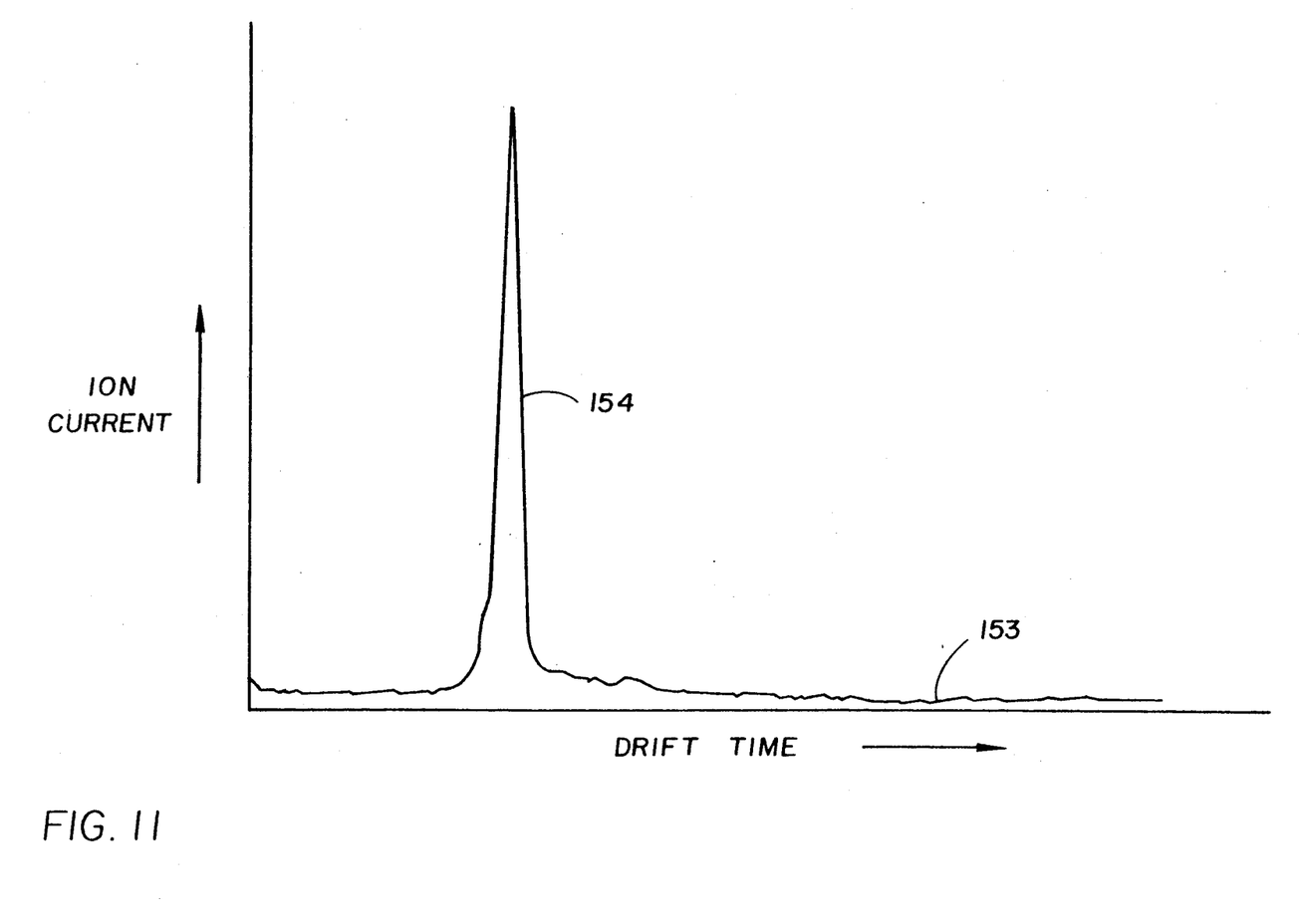
FIGS. 11 and 12 are graphs showing the operation of the embodiments in FIGS. 7 and 9.
Figure 12:
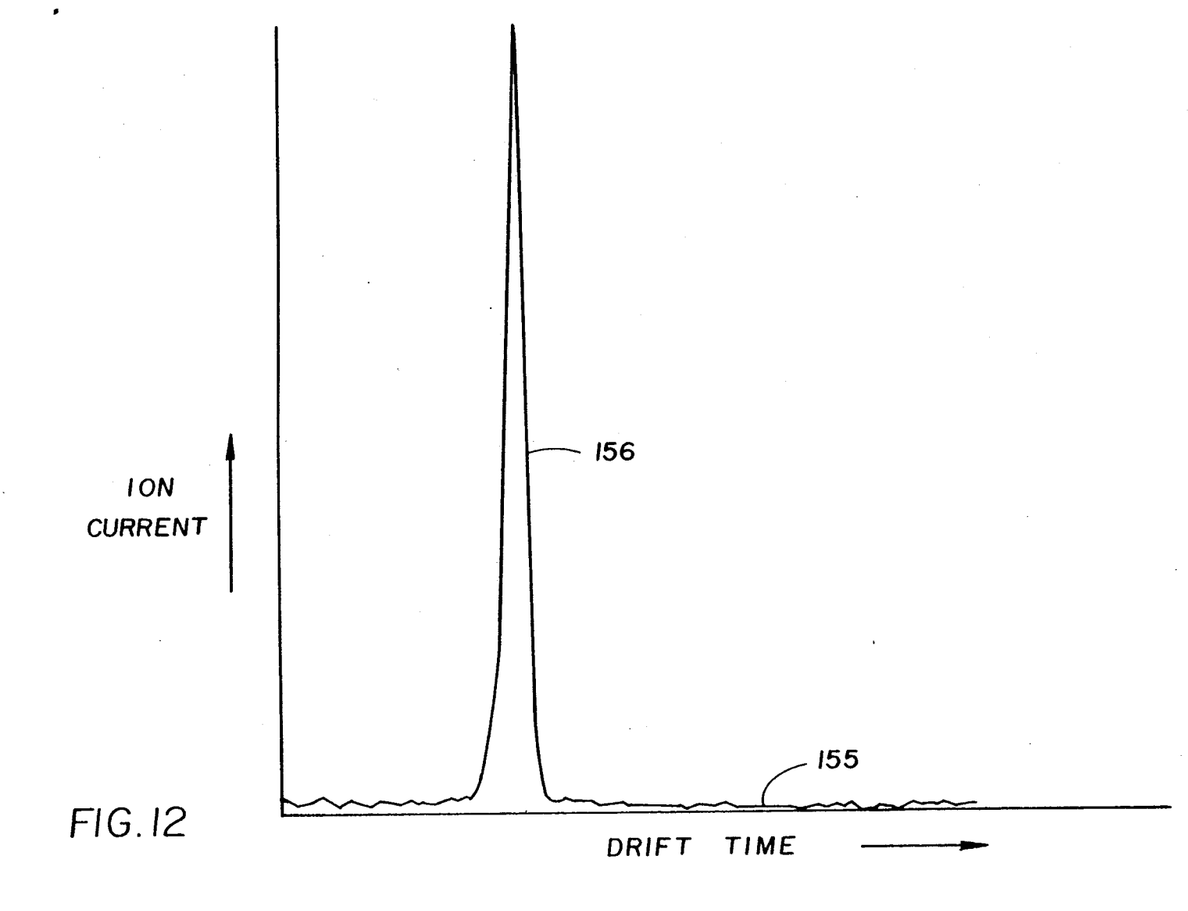

FIGS. 11 and 12 is a graph showing the operation of IMS 10' and 10''' in FIGS. 7 and 9 wherein ionization source 44' includes radioactive metal foil 130. In FIGS. 11 and 12 the ordinate represents ion current and the abscissa represents ion drift time. Drift time is the time for ions to move from shutter grid assembly 18 or shutter grid 142 to collector 34. In FIG. 11, ion mobility spectrum or curve 153 shows the output of the IMS cell to the positive reactant ions without sample gas 82. Peak 154 is due to the positive reactant ion. In FIG. 12 ion mobility spectrum or curve 155 shows the output of the IMS cell due to negative reactant ions without sample gas 82. Peak 156 is due to the negative reactant ion.

What is claimed is:

1. An ion mobility spectrometer comprising:
   a block of ceramic material having a passageway therethrough containing a reaction region, a shutter grid assembly, a drift region, an aperture grid, and a collector;
   said passageway having a longitudinal axis and a first length to form said reaction region beginning at a first end of said first length and extending to said shutter grid assembly;
   said passageway having a cross section from its first end for receiving and supporting an ionization source positioned in said reaction region;
   said first length of said passageway having portions thereof with a first resistive layer therein to form an electric field in the direction of said longitudinal axis at times a voltage is placed longitudinally across said first resistive layer to move ions formed in said first length to said shutter grid assembly, said shutter grid assembly positioned across said passageway at the second end of said first length;

said passageway having a second length to form a drift region extending from said shutter grid assembly to an aperture grid, said second length of said passageway having portions thereof with a second resistive layer therein to form an electric field in the direction of said longitudinal axis at times a voltage is placed longitudinally across said second resistive layer to move ions passing through said shutter grid assembly to said aperture grid, said aperture grid positioned across said passageway at the second end of said second length, said passageway having a third length having a first and second end extending from said aperture grid to a collector, respectively;

said passageway having a cross section from its second end of said passageway for receiving said aperture grid for positioning at said first end of said third length and for receiving said collector for positioning at said second end of said third length;

first means for introducing a drift gas into said drift region; and second means for introducing a carrier gas including a sample gas to be detected into said reaction region.

2. The ion-mobility spectrometer of claim 1 wherein said shutter grid assembly comprises a first and second grid spaced apart by a spacer, said first and second grid having a predetermined cross section to fit against an annular ledge at a predetermined location in said passageway, each shutter grid having a tab for extending through the wall between said passageway and the external surface of the block of ceramic material.

3. An ion-mobility spectrometer of claim 2 wherein said passageway is sealed where said shutter grid tabs extend through the wall of said passageway by a bead of adhesive.

4. The ion-mobility spectrometer of claim 2 wherein said shutter grid assembly is held in place by a cylinder inserted into the passageway against said shutter grid assembly.

5. The ion-mobility spectrometer of claim 4 wherein said cylinder further includes adhesive to hold said cylinder in place.

6. The ion-mobility spectrometer of claim 1 further including a ceramic retainer having sidewalls for fitting in said passageway and wherein the periphery of said sidewalls extend beyond a center region of said ceramic block which is machined- to receive a collector.

7. The ion-mobility spectrometer of claim 6 wherein said ceramic retainer has slots in said peripheral walls that extend beyond said collector whereby drift gas may pass through.

8. The ion-mobility spectrometer of claim 1 wherein said collector has a first conic shape attached to a rod which extends through said ceramic retainer and wherein said ceramic retainer has a conic cut out to receive said conic section of said collector.

9. The ion-mobility spectrometer of claim 8 wherein said collector is cemented to said ceramic retainer and wherein said ceramic retainer is positioned against said aperture grid and in contact with said aperture grid at peripheral extensions of said ceramic retainer with respect to said collector.

10. The ion-mobility spectrometer of claim 1 wherein said passageway has an annular ledge for receiving said aperture grid and wherein said inner surfaces of said passageway from said second end up to said annular ledge are coated with resistive material to provide electrical contact to said aperture grid.

11. The ion-mobility spectrometer of claim 1 wherein said ionization source is positioned on a ceramic plug.

12. The ion-mobility spectrometer of claim 11 wherein said ceramic plug has peripheral sidewalls extending a sufficient distance to be in contact with said shutter grid assembly whereby said shutter grid assembly is held in place.

13. The ion-mobility spectrometer of claim 12 further including a passageway in said ceramic plug to receive a metal foil of radioactive material.

14. The ion-mobility spectrometer of claim 12 wherein the inside surface of said peripheral side walls includes said first resistive layer.

15. The apparatus of claim 1 wherein said shutter assembly includes wires fed through holes in the wall of said passageway and through said passageway.

16. The ion-mobility spectrometer of claim 1 wherein said shutter assembly includes a plurality of holes formed through said block of ceramic material and wires fed through said holes wherein said holes are positioned in a row whereby wires fed through said holes pass through said passageway.

17. The apparatus of claim 16 wherein every other wire is electrically connected to a first pad and wherein the other wires are connected to a second pad.

18. The ion-mobility spectrometer of claim 17 wherein said wires are soldered to said pads and wherein said holes are sealed by adhesive.

19. The ion-mobility spectrometer of claim 18 wherein said holes lie in a plane transverse to the longitudinal axis of said passageway at the location of said holes.

20. The ion-mobility spectrometer of claim 1 further including a second ceramic block having a surface for mating with said block of ceramic material for injecting carrier gas and a sample gas through a passageway in the wall of said block of ceramic material.

21. The apparatus of claim 20 wherein said second block of ceramic material includes a heater for heating a sample gas and carrier gas prior to entry into the reaction region.

22. The ion-mobility spectrometer of claim 20 wherein said second ceramic block further includes a membrane in a cavity having one side of said membrane exposed to inlet sample gas and the other side of said membrane exposed to carrier gas which is coupled over a second passageway into said reaction region.

23. An ion mobility spectrometer, comprising:
a ceramic block defined by a passageway therethrough, said passageway being subdivided into a reaction region and a drift region;
a shutter grid separating the reaction region from the drift region of said passageway;
an ionization source coupled to one end of said ceramic block and extending into the reaction region of said passageway;
an aperture grid arranged proximate to another end of said ceramic block within said passage way;

a collector inserted into said passageway at said other end of said ceramic block and abutting said aperture grid;

ceramic retaining means for sealably retaining said collector in said passageway.

24. The ion mobility spectrometer of claim 23, wherein said ceramic block is further defined by a plurality of holes penetrating the periphery of said ceramic block and extending radially inward to said passageway, and said shutter grid further comprises a wire threaded through the holes in said ceramic block to form a grid pattern transverse to said passageway.

25. The ion mobility spectrometer of claim 23, wherein said ionization source is radioactive.

26. The ion mobility spectrometer of claim 23, wherein said ionization source is non-radioactive.

27. The ion mobility spectrometer of claim 23, wherein said ionization source further comprises a ceramic plug for sealably fitting within the passageway at said one end of said ceramic block and extending into the reaction region of said passageway, a thermionic emitter arranged proximate to said plug within the reaction region of said passageway, connecting means for providing an electrical connection to said thermionic emitter through said plug.

28. The ion mobility spectrometer of claim 23, wherein said aperture grid further comprises a washer defined by a central hole, and a plurality of resistive wires attached to said washer at the perimeter of said hole to form a grid pattern spanning said hole.

29. The ion mobility spectrometer of claim 23, wherein said ceramic block further comprises a resistive layer within said passageway and enclosing said reaction region for generating an electric field therein, and connecting means for providing an electrical connection to said resistive layer through said block.

30. The ion mobility spectrometer of claim 29, wherein said connecting means further comprises a plurality of contact pads arranged external to said ceramic block, and a plurality of conductive ink paths corresponding to said contact pads.

* * * * *